(12) United States Patent
Felber

(10) Patent No.: US 10,434,229 B2
(45) Date of Patent: Oct. 8, 2019

(54) BREAST PUMP UNIT

(71) Applicant: MEDELA HOLDING AG, Baar (CH)

(72) Inventor: Armin Felber, Lucerne (CH)

(73) Assignee: MEDELA HOLDING AG, Baar (CH)

( * ) Notice: Subject to any disclaimer, the term of this patent is extended or adjusted under 35 U.S.C. 154(b) by 113 days.

(21) Appl. No.: 14/903,810

(22) PCT Filed: Jul. 14, 2014

(86) PCT No.: PCT/EP2014/065024
§ 371 (c)(1),
(2) Date: Jan. 8, 2016

(87) PCT Pub. No.: WO2015/007679
PCT Pub. Date: Jan. 22, 2015

(65) Prior Publication Data
US 2016/0151551 A1    Jun. 2, 2016

(30) Foreign Application Priority Data

Jul. 16, 2013 (CH) ........................ 1267/13

(51) Int. Cl.
*A61M 1/06* (2006.01)

(52) U.S. Cl.
CPC .............. *A61M 1/062* (2014.02); *A61M 1/06* (2013.01); *A61M 1/064* (2014.02); *A61M 2205/3341* (2013.01); *A61M 2205/3344* (2013.01)

(58) Field of Classification Search
CPC ........ A61M 1/06; A61M 1/062; A61M 1/064; A61M 1/066; A61M 1/068
See application file for complete search history.

(56) References Cited

U.S. PATENT DOCUMENTS

| | | | |
|---|---|---|---|
| 6,358,226 B1 * | 3/2002 | Ryan | A61M 1/062 604/113 |
| 6,383,163 B1 * | 5/2002 | Kelly | A61M 1/06 604/118 |

(Continued)

FOREIGN PATENT DOCUMENTS

| | | |
|---|---|---|
| CN | 101730554 A | 6/2010 |
| WO | WO-01/47577 A2 | 7/2001 |

(Continued)

OTHER PUBLICATIONS

English Translation of International Preliminary Report on Patentability for International Application No. PCT/EP2014/065024, dated Jan. 19, 2016.

(Continued)

*Primary Examiner* — Nathan R Price
*Assistant Examiner* — Dung T Ulsh
(74) *Attorney, Agent, or Firm* — Marshall, Gerstein & Borun LLP

(57) ABSTRACT

A breastpump unit for expressing human breastmilk has a breastshield for placing on a human mother's breast, a vacuum pump for generating an underpressure, and a suction line for connecting the breastshield to the vacuum pump and for transferring to the breastshield the underpressure generated by the vacuum pump. The breastpump unit also has a pressure sensor. In addition, a measuring line is present, wherein the measuring line extends from the breastshield to the pressure sensor.

13 Claims, 3 Drawing Sheets

(56) References Cited

U.S. PATENT DOCUMENTS

| | | | | |
|---|---|---|---|---|
| 7,223,255 B2* | 5/2007 | Myers | A61M 1/06 604/74 |
| 8,052,635 B1* | 11/2011 | Kelly | A61M 1/0037 604/74 |
| 8,137,305 B2* | 3/2012 | Kelly | A61M 1/0037 604/74 |
| 9,603,982 B2* | 3/2017 | Silver | A61M 1/06 |
| 2003/0073951 A1* | 4/2003 | Morton | A61B 5/6834 604/73 |
| 2003/0204164 A1* | 10/2003 | Britto | A61M 1/06 604/74 |
| 2004/0133151 A1* | 7/2004 | Watanabe | A61M 1/06 604/74 |
| 2005/0137539 A1* | 6/2005 | Biggie | A61M 1/0096 604/313 |
| 2006/0211335 A1* | 9/2006 | Lantz | A61M 1/06 450/38 |
| 2007/0060873 A1* | 3/2007 | Hiraoka | A61M 1/0066 604/74 |
| 2008/0009815 A1* | 1/2008 | Grabenkort | A61M 1/0031 604/346 |
| 2008/0177224 A1* | 7/2008 | Kelly | A61M 1/0037 604/74 |
| 2008/0255503 A1* | 10/2008 | Quackenbush | A61M 1/0031 604/74 |
| 2009/0099511 A1* | 4/2009 | Sutrina | A61M 1/0031 604/74 |
| 2011/0004154 A1* | 1/2011 | Van Schijndel | A61M 1/06 604/74 |
| 2011/0071466 A1* | 3/2011 | Silver | A61M 1/06 604/74 |
| 2011/0106027 A1* | 5/2011 | Vess | A61M 1/0023 604/319 |
| 2011/0178481 A1* | 7/2011 | Locke | A61M 1/0088 604/319 |
| 2011/0251552 A1* | 10/2011 | Brittner | A61M 1/06 604/74 |
| 2012/0271256 A1* | 10/2012 | Locke | A61M 1/0088 604/319 |
| 2012/0277636 A1* | 11/2012 | Blondheim | A61B 5/11 600/595 |
| 2013/0023821 A1* | 1/2013 | Khalil | A61M 1/064 604/74 |
| 2014/0031744 A1* | 1/2014 | Chen | A61M 1/06 604/74 |
| 2014/0052106 A1* | 2/2014 | Sherman | A61J 9/00 604/514 |
| 2014/0094748 A1* | 4/2014 | Hong | A61M 1/062 604/74 |
| 2014/0121593 A1* | 5/2014 | Felber | A61M 1/06 604/74 |
| 2014/0128806 A1* | 5/2014 | Schlienger | A61M 1/06 604/74 |
| 2014/0227112 A1* | 8/2014 | Felber | A61M 1/0066 417/53 |
| 2014/0235958 A1* | 8/2014 | Addington | A61J 15/0046 600/301 |
| 2014/0323962 A1* | 10/2014 | Kooijker | A61M 1/06 604/74 |
| 2014/0330200 A1* | 11/2014 | Scheidegger | A61M 1/06 604/74 |
| 2014/0373842 A1* | 12/2014 | Ahmad | A61M 16/1075 128/204.15 |
| 2015/0190560 A1* | 7/2015 | Aalders | A61M 1/06 604/514 |
| 2015/0231316 A1* | 8/2015 | Aalders | A61M 1/06 604/74 |
| 2015/0238669 A1* | 8/2015 | Aalders | A61M 1/0072 604/74 |
| 2015/0250932 A1* | 9/2015 | Kessels | A61M 1/06 604/74 |
| 2015/0265753 A1* | 9/2015 | Prentice | A61M 1/0031 604/74 |
| 2015/0328380 A1* | 11/2015 | Furrer | A61M 1/0049 604/74 |
| 2015/0335800 A1* | 11/2015 | Yamashita | A61M 1/06 604/74 |

FOREIGN PATENT DOCUMENTS

| | | |
|---|---|---|
| WO | WO-2011/037841 A2 | 3/2011 |
| WO | WO-2011/144984 A1 | 11/2011 |
| WO | WO-2012/157895 A2 | 11/2012 |
| WO | WO-2013/049944 A1 | 4/2013 |

OTHER PUBLICATIONS

Written Opinion for International Application No. PCT/EP2014/065024, dated Oct. 9, 2014.

International Search Report for Application No. PCT/EP2014/065024, dated Oct. 9, 2014.

* cited by examiner

BREAST PUMP UNIT

CROSS-REFERENCE TO RELATED APPLICATION

The present application is the US national phase of International Patent Application No. PCT/EP2014/065024, filed Jul. 14, 2014, which application claims priority to Switzerland Application No. 1267/13, filed Jul. 16, 2013. The priority application, CH 1267/13, is hereby incorporated by reference.

FIELD OF THE DISCLOSURE

The present invention relates to a breastpump unit for expressing human breastmilk and to a breastshield of such a breastpump unit.

PRIOR ART

Manually operated breastpumps and also motor-driven breastpumps are known in the prior art. The breastpumps provided with an electric motor can be connected to a mains supply or can be battery-operated. These breastpumps comprise a vacuum pump, and one or two breastshields which are connected to the vacuum pump and are placed on one or both of the mother's breasts. The connection can be direct, i.e. the vacuum pump is arranged on the breastshield itself, or the vacuum pump and the breastshield are connected to each other via a suction hose, also called a vacuum hose. By means of the vacuum pump, an underpressure can be generated in the breastshield, as a result of which milk is sucked from the mother's breast.

The breastshield is connected to a milk collection container, in which the expressed milk is collected. Milk collection containers can be bags or bottles, which are able to be connected in an airtight manner to a corresponding outlet of the breastshield. A known breastpump unit is described in WO 01/47577, for example.

In order to limit the generated underpressure, some of the motor-driven and electronically controlled vacuum pumps have a pressure sensor. Examples of these are disclosed in U.S. Pat. Nos. 6,383,163, 8,137,305 and U.S. 2008/0009815. These pressure sensors each measure the pressure in the area of the suction line near the pump, or at the suction connector of the vacuum pump itself. U.S. 2007/0060873 discloses a breastshield with a vacuum pump fitted thereon, wherein the vacuum pump is equipped with a media separation membrane and with a pressure indicator.

WO 2013/049944 proposes using the suction hose also as a milk line. A media separation membrane between the pump-side end of the suction hose and the vacuum pump protects the vacuum pump from contamination by milk. This media separation membrane is provided with a pressure sensor, in order to determine the pressure in this area.

WO 2011/037841 proposes arranging a pressure sensor in the breastshield itself and connecting it via an electronic line to a control unit or controller of the vacuum pump. However, breastshields are products to be disposed of after one use or, if designed to be used more than once, are at least not designed for prolonged use. They therefore have to be inexpensive. If designed to be used more than once, they also need to be easy to clean, and therefore pressure sensors inside or on top of the breastshield get in the way.

WO 2011/144984 discloses a device intended for directly breastfeeding a baby. This device also comprises a vacuum pump for generating an underpressure, and a breastshield for placing on a human mother's breast. The breastshield in this case ends in a milk receptacle, which is connected via a line to a teat for the baby. Milk is firstly expressed by means of the vacuum pump and collected in the milk receptacle. The vacuum pump is then stopped. If the baby now begins sucking, a vacuum sensor determines a drinking underpressure and, by way of a control unit, allows a valve to open in order to return the underpressure in the milk receptacle to atmospheric pressure. The baby is then able to suck. For as long as the drinking underpressure is detected, the vacuum pump remains inactive.

DISCLOSURE OF THE INVENTION

It is an object of the invention to optimize the measurement of pressure during the expression of human breastmilk.

The breastpump unit according to the invention for expressing human breastmilk has a breastshield for placing on a human mother's breast, a vacuum pump for generating an underpressure, and a suction line for connecting the breastshield to the vacuum pump and for transferring to the breastshield the underpressure generated by the vacuum pump. A pressure sensor is also present. According to the invention, a measuring line is additionally present, wherein the measuring line extends from the breastshield to the pressure sensor. It preferably ends at the pressure sensor.

By virtue of the unit according to the invention, the pressure can be measured at the site of the desired action of the breastpump, namely in the area near the mother's breast. Nonetheless, the breastshields do not have to be equipped with expensive sensors.

The arrangement according to the invention, with the separate and in particular air-filled measuring line, can be used in all known breastpump units. However, it is advantageous particularly in breastpump units in which the suction hose is also used as a milk line. Since a liquid column is therefore present in the suction hose and changes depending on the position of the suction hose, this can lead to an incorrect pressure measurement. The use of a separate, air-filled measuring line, preferably a measuring hose, guarantees an accurate measurement of the pressure, independently of the position of the vacuum pump, the length of the suction hose, and the position of the suction hose and of the measuring hose.

In a preferred embodiment, the pressure sensor is arranged in the breastpump. The breastpump has a housing which accommodates the vacuum pump, an electronic control unit for controlling the vacuum pump, operating means for operating the electronic control unit, possibly display means, and also the pressure sensor.

In a very simple embodiment, the pressure sensor serves only as a safety element, ensuring that an excessive underpressure is not applied. Alternatively or in addition, the safety element can serve to determine whether an underpressure is in fact present at all in the breastshield. If, for example, the breastshield is not placed tightly enough on the mother's breast, a warning signal can sound or an optical signal can displayed.

In a preferred embodiment, the electronic control unit for controlling the vacuum pump is connected to the pressure sensor. In this way, the vacuum pump can be controlled according to the measured pressure values inside the breastshield, and the underpressure applied to the mother's breast is optimized. In a preferred embodiment, the pressure sensor also assumes one or both of the abovementioned safety functions.

The measuring line and the suction line are preferably hoses, in particular flexible hoses. They can be made from silicone, for example. In a preferred embodiment, the measuring line and the suction line are designed together as a double-lumen hose. This facilitates the plugging in and the general handling of the breastpump unit.

In a preferred embodiment, the suction line has a first breastshield-side end, and the measuring line has a second breastshield-side end, wherein these two ends extend separately from each other. This makes it easier to plug in the hoses and to equip the breastshield with a protective element or media separation device described below.

The underpressure is usually generated in a suction chamber of the breastshield, wherein the underpressure in this suction chamber can be measured. In one embodiment, the measuring line opens into this suction chamber. In this way, measurement is actually carried out on the spot, i.e. at the place where the nipple of the mother's breast is also located.

A protective element is preferably present, which separates the measuring line from an interior of the breastshield to which expressed breastmilk can be admitted. In this way, the measuring line and thus also the pressure sensor are protected from contamination with breastmilk. The protective element is impermeable to liquid. It can be an air-permeable filter, or an element that is impermeable to air and liquid.

A media separation device is preferably present, which separates the measuring line from an interior of the breastshield, but which transfers pressure changes in the interior to the measuring line. The media separation device is preferably a flexible, fluid-impermeable membrane of the kind already also used in other areas of breastpump units, e.g. at the vacuum port of the breastpump and also at the breastshield-side connection of the suction hose. The interior is preferably the abovementioned suction chamber. The media separation device is preferably the abovementioned protective element.

To ensure that the breastshield can be easily cleaned, or can be disposed of after use, the measuring line is preferably releasably connectable to the breastshield several times. In this way, the measuring line, but in particular the pressure sensor, can be used more than once. Alternatively, the measuring line is not connected to the breastshield free from destruction, but is easily releasable from the pressure sensor, without damaging the latter.

The breastshield according to the invention has a first seat for receiving a suction line, and a second seat for receiving a measuring line.

With a suitable design of a double-lumen suction and measuring hose, the latter can be plugged into a single opening of the breastshield. Preferably, the first seat is a suction opening for receiving a suction hose, and the second seat is a separate measurement opening for receiving a measuring line. The second seat is preferably provided with a media separation device.

Further embodiments are set forth in the dependent claims.

BRIEF DESCRIPTION OF THE DRAWINGS

Preferred embodiments of the invention are described below with reference to the drawings, which are provided only for explanatory purposes and are not to be interpreted as limiting the invention. In the drawings.

DESCRIPTION OF PREFERRED EMBODIMENTS

Figure 1:
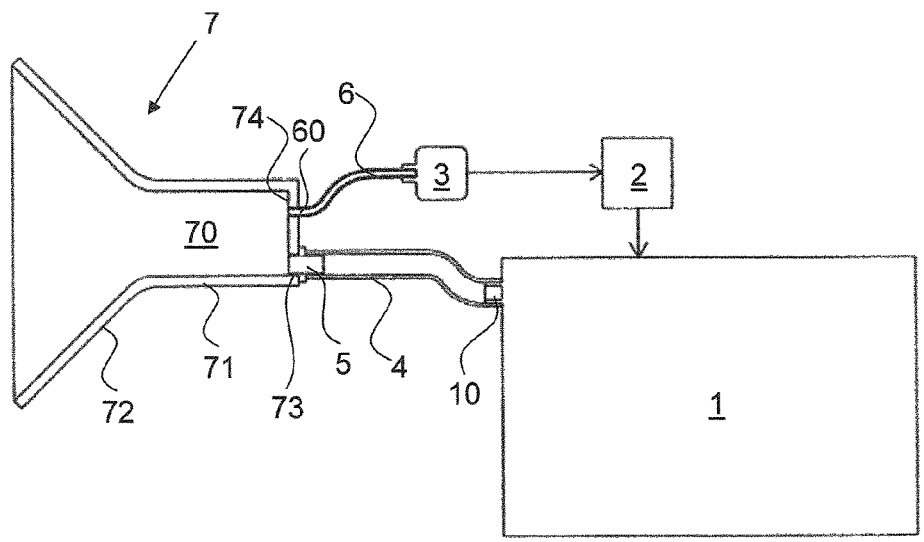
FIG. 1 shows a schematic view of a breastpump unit according to the invention in a first embodiment.

FIG. 1 shows a first example of a breastpump unit according to the invention. A vacuum pump 1 has a suction connector 10. A suction line, here a suction hose 4, is connected to this suction connector 10. The suction hose 4 is preferably a conventional silicone hose of the kind used customarily in breastpump units.

The breastpump unit further comprises one or two breastshields 7 for placing on a human mother's breast. The breastshield 7 can be of the types known in the prior art. The shape and configuration shown are provided only by way of illustration.

The breastshield 7 shown here has a stub 71 and, formed integrally on the latter, an outwardly widening funnel 72. The latter receives the mother's breast. Depending on the configuration of the breastshield, it is possible for the nipple of the mother's breast to protrude into the stub 71. The breastshield 7 has an interior 70, and a first opening 73 leading out from this interior 70. The abovementioned suction hose 4 can be plugged with its first breastshield-side end 40 into this first opening 73 or can be connected otherwise to a seat formed via the first opening 73. In these figures, an adapter 5 is provided for plugging in.

A milk collection container is not shown. It can be mounted directly on the breastshield in a known way. However, the suction line can also serve at the same time as a milk line, such that the milk collection container is filled via a line (not shown) leading from the element 1. This combination of suction line and milk line is disclosed in WO 2013/049944.

The breastshield 7 has a second opening 74, which likewise leads out from the interior 70. From this seat or opening 74, a measuring line 6 leads to a pressure sensor 3. The measuring line 6 is preferably likewise a hose, for example a silicone hose. However, it preferably has a smaller diameter than the suction hose 4. The measuring hose 6 is preferably filled with air.

In this example, a second breastshield-side end 60 of the measuring hose 6 is plugged into the second opening 74. It can also be connected to the breastshield 7 in another way. Preferably, the connection between measuring line 6 and breastshield 7 is designed such that it can be released and then brought together again. If measuring line 6 and breastshield 7 are not releasable from each other without destruction, then the connection between measuring line 6 and sensor 3 is preferably releasable, without damaging the sensor 3 or the sensor-side plug connection.

Figures 6, 7:
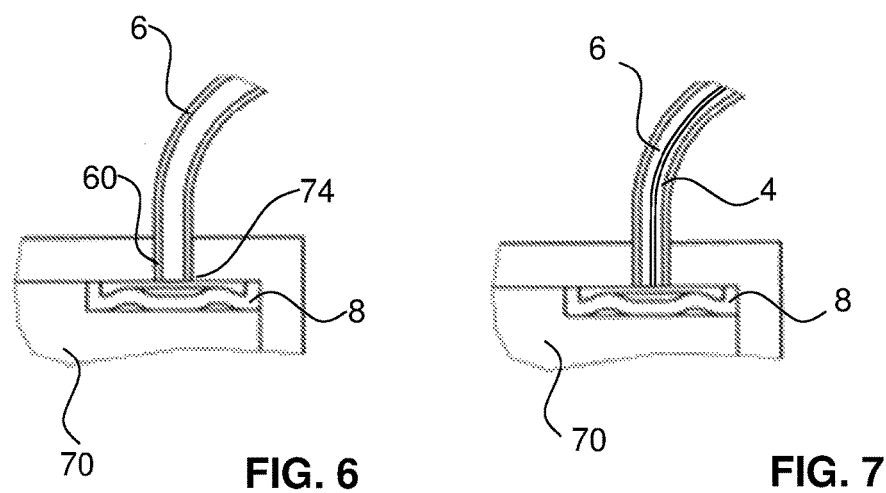
FIG. 6 shows an enlarged detail as per FIG. 5.
FIG. 7 shows an enlarged detail of a breast pump unit according to the invention in a fifth embodiment.

In these examples, the suction hose 4 and the measuring hose 6 are shown as hoses extending separately from each other. However, a double-lumen hose can also be used as shown in FIG. 7.

Known sensors, for example piezoelectric sensors, are suitable as pressure sensor 3. The pressure sensor is connected to an electronic control unit 2 of the vacuum pump.

The lines between control unit 2 and pressure sensor 3 and between control unit 2 and vacuum pump 1 are provided with arrows here.

Vacuum pump 1, control unit 2 and pressure sensor 3 are preferably arranged, together with manual operating means and a possible display or screen, in a common housing. The housing is not shown here. The breastshield 7 is separate from this housing, with the suction line 4 and the measuring line 6 leading from the housing to the breastshield 7.

Independently of the position of the milk line and the position of the suction line 4, the pressure sensor 3 now measures the pressure in the interior 70 of the breastshield, i.e. at the place where an underpressure is generated via the vacuum pump and where the nipple is also located. The measured signal is fed to the control unit 2 which, depending on the configuration of the control unit, triggers one or more of the following actions:

- display of the pressure value on a screen (not shown here),
- optical display or acoustic signal when a predefined minimum or maximum value is undershot or exceeded,
- automatic adaptation of the underpressure generated by the vacuum pump at the suction connector 10,
- switching-off of the vacuum pump in the event of a maximum value being exceeded, i.e. when the applied underpressure in absolute values becomes too high or, to put it another way, when the suction is too great.

In the example according to FIG. 1, the first and second openings 73, 74 are arranged on the same side of the breastshield 7, in this case on the end face of the stub 71 directed away from the breast.

Figure 2:
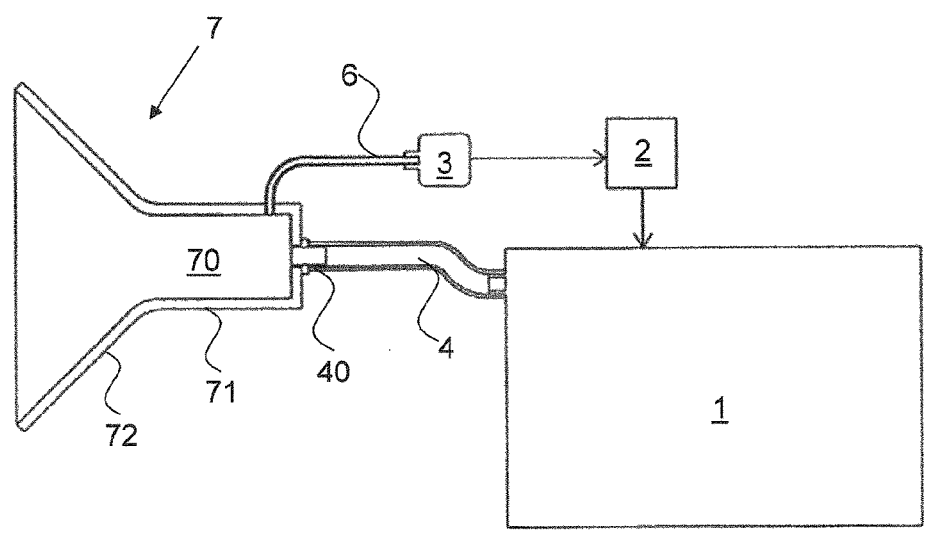
FIG. 2 shows a schematic view of a breastpump unit according to the invention in a second embodiment.
Figure 3:
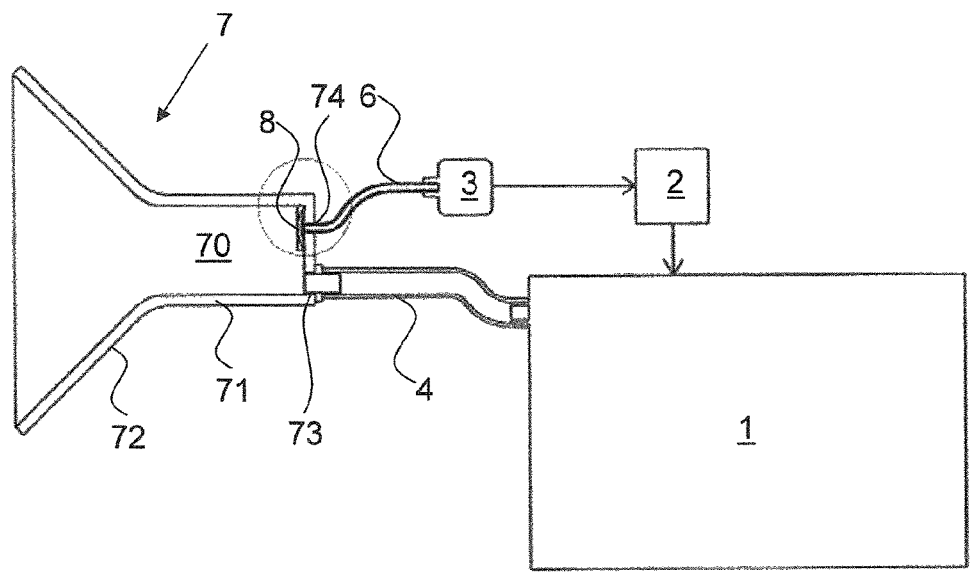
FIG. 3 shows a schematic view of a breastpump unit according to the invention in a third embodiment.
Figure 4:
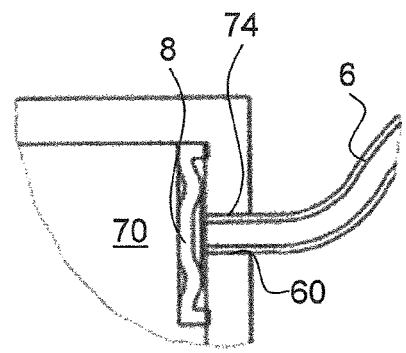
FIG. 4 shows an enlarged detail as per FIG. 3.
Figure 5:
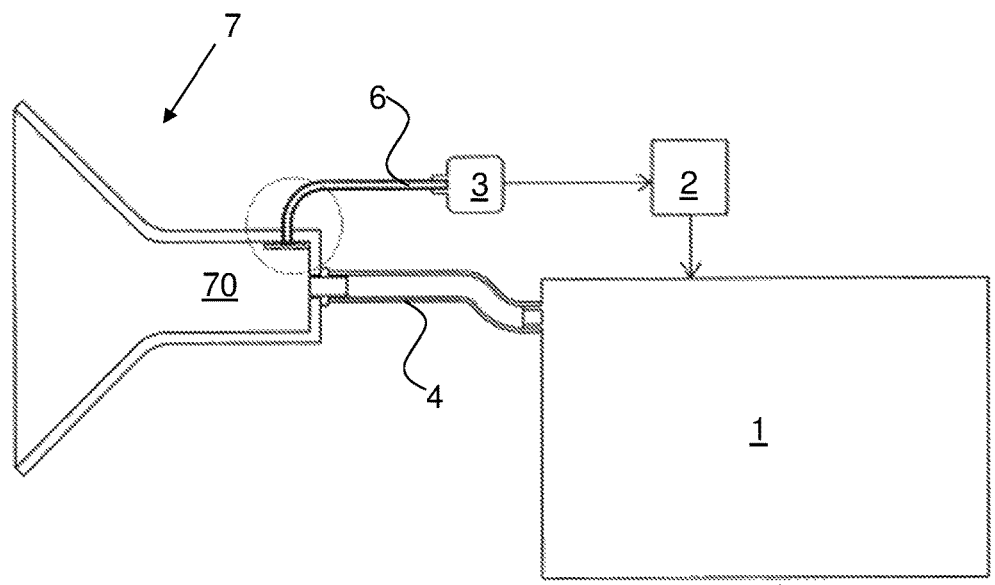
FIG. 5 shows a schematic view of a breastpump unit according to the invention in a fourth embodiment.

In the variant according to FIG. 2, the first opening 73 is again arranged in the end face of the stub 71 directed away from the breast. The second opening 74 is located at an angle of 90° thereto on the circumference of the stub 71.

In the examples according to FIGS. 1 and 2, the measuring line 6 leads directly, and without intermediate elements, into the interior 70. However, the interior 70 can be provided with a liner, for example.

The embodiments according to FIGS. 3 to 6 correspond to those described above. However, they have a protective element in the form of a media separation membrane 8 in the area of the second opening 74. The media separation membrane 8 is liquid-tight and preferably also airtight. It is preferably made from silicone or another flexible material.

In these examples, the media separation membrane 8 is secured in the interior 70 on the inside face of the stub 71. It can be arranged in a housing, for example, or can simply be affixed to the wall of the stub 71 or welded thereto. However, it can also be removable, for example in order to be cleaned.

The media separation membrane 8 is preferably flat and round. It has circular elevations and depressions, in order to move when the underpressure changes. In this way, it transfers pressure changes in the interior 70 to the measuring line 6 and thus to the pressure sensor 3. At the same time, it prevents expressed milk and bacteria or other contaminants from getting into the measuring line.

The media separation membrane can also be arranged on the outside of the breastshield or on the second breastshield-side end 60 of the measuring line 6.

The breastpump unit according to the invention permits, in a cost-effective manner, a relatively precise measurement of the underpressure applied to the mother's breast.

The invention claimed is:

1. A breastpump unit for expressing human breastmilk, wherein the breastpump unit has a breastshield for placing on a human mother's breast, the breastshield defining an interior configured to receive the human mother's breast, the breastpump unit further comprising a vacuum pump for generating an underpressure, and a suction line having a first lumen, the first lumen connecting the breastshield to the vacuum pump and transferring the underpressure generated by the vacuum pump to the interior of the breastshield, wherein the breastpump unit also has a pressure sensor, wherein a measuring line with a second lumen is additionally present, and wherein the breastshield has an opening and wherein the second lumen of the measuring line extends from the opening of the breastshield to the pressure sensor, the second lumen of the measuring line being used for detecting a pressure in the interior of the breastshield with the pressure sensor, wherein the second lumen is separate from the first lumen along a whole length of the second lumen from the breastshield to the pressure sensor and along a whole length of the first lumen from the breastshield to the vacuum pump, wherein a protective element is present in an area of the opening, the protective element separating the measuring line from the interior of the breastshield into which expressed breastmilk can be admitted, wherein the protective element is a media separation device, which transfers pressure changes in the interior of the breastshield to the measuring line so that the pressure in the interior of the breastshield can be measured.

2. The breastpump unit according to claim 1, further comprising an electronic control unit for controlling the vacuum pump, and wherein the pressure sensor is connected to the electronic control unit.

3. The breastpump unit according to claim 1, wherein the measuring line and the suction line are hoses.

4. The breastpump unit according to claim 1, wherein the measuring line and the suction line are designed together as a double-lumen hose.

5. The breastpump unit according to claim 1, wherein the suction line has a first breastshield-side end, and the measuring line has a second breastshield-side end, and wherein the first breastshield-side end and the second breastshield-side end extend separately from each other.

6. The breastpump unit according to claim 1, wherein the underpressure can be generated in a suction chamber of the breastshield, and wherein the underpressure in the suction chamber can be measured by the pressure sensor via the measuring line.

7. The breastpump unit according to claim 6, wherein the measuring line opens into this suction chamber.

8. The breastpump unit according to claim 6, wherein the interior is the suction chamber.

9. The breastpump unit according to claim 1, wherein the media separation device is a flexible, fluid-impermeable membrane.

10. The breastpump unit according to claim 1, wherein the measuring line is releasably connectable to the breastshield several times.

11. The breastpump unit according to claim 1, wherein the measuring line ends at the pressure sensor.

12. A breastshield of the breastpump unit according to claim 1, wherein the breastshield has a first seat for receiving the suction line, and a second seat for receiving the measuring line.

13. The breastshield according to claim 12, wherein the first seat is a first opening for receiving a suction hose, and the second seat is a second opening for receiving a measuring hose.

* * * * *